United States Patent [19]

Smith

[11] 4,011,244
[45] Mar. 8, 1977

[54] PROCESS FOR PREPARING TETRAHYDROFURAN

[75] Inventor: William Edward Smith, Schenectady, N.Y.

[73] Assignee: General Electric Company, Pittsfield, Mass.

[22] Filed: Oct. 20, 1975

[21] Appl. No.: 623,904

Related U.S. Application Data

[63] Continuation-in-part of Ser. No. 420,851, Dec. 3, 1973, abandoned.

[52] U.S. Cl. .......................................... 260/346.1 R
[51] Int. Cl.$^2$ ...................................... C07D 307/08
[58] Field of Search ............................ 260/346.1 R

[56] References Cited

FOREIGN PATENTS OR APPLICATIONS 2,062,950 7/1971 Germany
1,170,222 12/1969 United Kingdom ........ 260/346.1 R Primary Examiner—Henry R. Jiles
Assistant Examiner—Bernard Dentz
Attorney, Agent, or Firm—Donald M. Papuga; William F. Mufatti

[57] ABSTRACT

A process for preparing tetrahydrofuran which comprises heating a carboxylic acid monoester of 1,4-butanediol in the vapor phase in the presence of a dehydroacyloxylation catalyst.

2 Claims, No Drawings

PROCESS FOR PREPARING TETRAHYDROFURAN

This application is a continuation-in-part application of Patent Application Ser. No. 420,851, filed Dec. 3, 1973, and now abandoned.

This invention relates to a process for preparing tetrahydrofuran which comprises heating a carboxylic acid monoester of 1,4-butanediol in the vapor phase in the presence of a dehydroacyloxylation catalyst.

BACKGROUND OF THE INVENTION

It is known in the art that tetrahydrofuran may be produced by a number of different methods, the more prominent among them the dehydration of 1,4-butanediol and the catalytic hydrogenation of furan. Most tetrahydrofuran is, in fact, manufactured in a multi-step sequence starting with the reaction of acetylene and formaldehyde in the presence of a cuprous acetylide complex to form butynediol. The butynediol is hydrogenated to butanediol, which is dehydrated to tetrahydrofuran as indicated above.

In addition, tetrahydrofuran can be prepared by catalytic hydrogenation of maleic, fumaric and succinic acids, their respective anhydrides and ester derivatives, and butyrolactone.

All of these methods involve the use of hazardous or expensive materials, and catalysts that are expensive in some instances and easily poisoned in others.

The liquid phase conversion of 1,4-butanediol carboxylate ester derivatives to tetrahydrofuran in the presence of strongly acidic catalysts and water has been described by Kohll in British Patent 1,170,222 and by Ono et al in German Offenlengungsschrift 2,062,950. These processes are characterized by low rates and extent of conversion and are not suitable for use under substantially anhydrous conditions.

Tetrahydrofuran is a useful solvent for natural and synthetic resins and is a valuable intermediate in manufacture of a number of chemicals and plastics.

DESCRIPTION OF THE INVENTION

It has been discovered that tetrahydrofuran may be advantageously prepared by heating a carboxylic acid monoester of 1,4-butanediol in the vapor phase in the presence of a heterogeneous dehydroacyloxylation catalyst. The method is characterized by high reaction efficiency; yields are essentially quantitative and a high conversion of the starting ester may be accomplished per pass. In addition, the method is applicable to conversion of 4-acetoxybutanol used in admixture with its diol and diacetate disproportionation products and the corresponding derivatives of the isomeric 1,2-butanediol and 2-methyl-1,3-propanediol systems. Furthermore, the process may be operated efficiently even under substantially anhydrous conditions in which case the diester derivative can be recovered essentially unchanged.

The process is illustrated for the case of 4-acetoxybutanol in Equation 1.

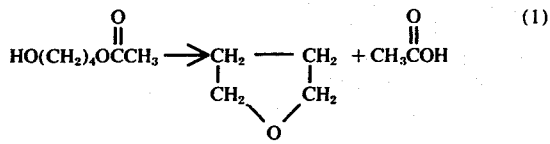

A class of dehydroacyloxylation catalysts particularly effective in promoting the ring closure and evolution of the carboxylic acid includes alumina, silica, silica-alumina, silica-magnesia, and other combinations in which either silica or alumina or their combination constitute the principal component. The silica-alumina dehydroacyloxylation catalysts which may be used vary in composition from pure silica to pure alumina whereas the silica-magnesias vary in composition from pure silica to predominantly magnesia. The catalysts of the instant invention do not include those activated by treatment with strong acid. Such catalysts when used in the disclosed process promote undesired side reactions and, in addition, rapidly lose their activity and physical integrity.

The carboxylic acid monoesters of 1,4-butanediol suitable for use in the disclosed process are those in which the carboxy function contains from one to six carbon atoms. A preferred monoester is 4-acetoxybutanol. In a preferred embodiment the 4-acetoxybutanol is used in admixture with its 1,4-butanediol and 1,4-butanediol diacetate disproportionation products and the corresponding monoacetate, diol and diacetate derivatives of 1,2-butanediol and 2-methyl-1,3-propanediol. As disclosed in copending application Ser. No. 581,265, filed on May 27, 1975, entitled A Process for Preparing Tetrahydrofuran and assigned to the same assignee as the present invention, such a mixture can be derived from propylene by way of allyl acetate and a hydroformylation-hydrogenation sequence.

The process may be carried out under substantially anhydrous conditions, in which case the 1,4-butanediol diacetate present in the feedstock remains substantially unconverted; or in the presence of water, in which case the diacetate present undergoes hydrolysis to the monoacetate which subsequently is converted to tetrahydrofuran and acetic acid. In both cases, any acetate derivatives of the 1,2-butanediol and 2-methyl-1,3-propanediol undergo dehydroacetoxylation reactions also, producing crotyl and methallyl alcohol derivatives, butadiene, other olefinic compounds and butyraldehyde, so that the total amount of acetic acid recovered can be significantly greater than the stoichiometric amount based on the 4-acetoxybutanol initially present.

In comparison, the liquid phase process is complicated by the disproportionation reaction illustrated in Equation 2. This process

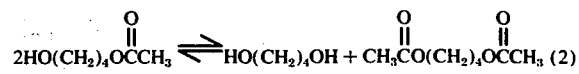

competes with tetrahydrofuran formation. The diol formed is easily converted to tetrahydrofuran but the diacetate formed is not. Therefore, a considerable excess of water must be present to hydrolyze the diacetate to the monoacetate so it can evolve acetic acid and form tetrahydrofuran. The vapor phase nature of the instant invention favors the intramolecular ring closure reaction and disfavors the intermolecular disproportionation reaction, so virtually all of the monoester can be converted to tetrahydrofuran directly, even under substantially anhydrous conditions. It is thus possible to convert 4-acetoxybutanol to tetrahydrofuran substantially free of its azeotrope with water.

The temperature at which the disclosed process can be carried out varies from about 200° C to about 325° C. Preferably, the reaction is carried out in the temperature range of from about 200° C to about 270° C. The maximum depends upon destruction of the product, olefin formation occurring from the 1,4-derivatives under too rigorous conditions.

In a preferred embodiment, a mixture of which 4-acetoxybutanol is the principal component is vaporized and passed through a fixed bed of the heated catalyst. The effluent is distilled to effect isolation of the tetrahydrofuran and acetic acid. Well-known techniques can be used to obtain the products in maximum yield and purity.

DESCRIPTION OF THE PREFERRED EMBODIMENT

The following examples are set forth to illustrate more clearly the principle and practice of this invention to those skilled in the art. Unless otherwise specified, where parts of percents are mentioned, they are parts or percents by weight.

Apparatus — A vertical hot tube reactor (16 mm ID × 70 cm effective length) is constructed from heavy wall glass, with 24/40 male and female joints. Vigreaux points are indented just above the male joint to support catalyst pellets. Thermocouple leads are fastened into three other Vigreaux indentations at points along the length. Three 4 ft. × 1 in. Briskheat glass insulated heating tapes are wound onto the tube, covered with glass wool and glass tape, and connected to separate variable transformers. The tube exit is connected by a gooseneck (also heated) to an efficient condenser and collection vessel. A three necked flask serves as the evaporator, with the reactants added from an addition funnel in a side neck. Nitrogen carrier gas is passed through to provide residence times on the order of 3 to 10 seconds.

EXAMPLE 1

The tube reactor described above is charged with 89 grams of silica-alumina catalyst (87% silica - 13% alumina, 3/16 inch × 3/16 inch pills, Davison Chemical Grade 970) and is maintained at 220° – 250° C. while 50.0 grams of a crude oxo product mixture containing, as indicated by quantitative glpc analysis, 31.7 grams of 4-acetoxybutanol, 10.2 grams of 1,4-butanediol diacetate, a very small amount of 1,4-butanediol, and oxo by-products (about 6 grams of acetate derivatives of 2-methyl-1,3-propanediol and 1,2-butanediol) is flash evaporated and passed through over one hour. Quantitative glpc analysis (propionic acid internal standard) of the effluent shows that no 4-acetoxybutanol remains unconverted, and that 17.3 grams of tetrahydrofuran (100% yield based on the 4-acetoxybutanol initially present) and 17.6 grams of acetic acid have been collected. The 1,4-butanediol diacetate passes through the tube essentially unchanged. Other products detected include the diacetates of the 1,2-butanediol and 2-methyl-1,3-propanediol, crotyl and methallyl alcohols and acetates, and butyraldehyde.

EXAMPLE 2

A 50.0 gram portion of the same crude oxo product mixture described in Example 1 is passed through the tube containing 85 grams of silica-magnesia catalyst (70% silica - 30% magnesia, 3/16 inch × 3/16 inch pills, Davison Chemical), again at 220°–250° C. and over a 1 hour period. The results, as indicated by quantitative glpc analysis of the effluent, are substantially the same as in Example 1 — 16.3 grams of tetrahydrofuran (94% yield) and 16.5 grams of acetic acid are collected.

EXAMPLE 3

The tube reactor is charged with 110 grams of alumina catalyst (⅛ inch pellets, Harshaw Al-0104T), which is subsequently subjected to pretreatment at 200° C. with 50% aqueous acetic acid. Then 50.0 grams of a crude oxo product mixture containing, as indicated by quantitative glpc analysis, 24.3 grams of 4-acetoxybutanol, 8.2 grams of 1,4-butanediol diacetate, and oxo by-products (about 5 grams of 3-acetoxy-2-methyl propanol, 6 grams of 2-acetoxybutanol, small amounts of the corresponding diacetates and acetic acid) is flash evaporated and passed through at 200°–220° C over 30 minutes. Quantitative glpc analysis of the effluent shows that no 4-acetoxybutanol remains unconverted and that 12.2 grams of tetrahydrofuran (92% yield based on the 4-acetoxybutanol) and 17.1 grams of acetic acid have been collected. The 1,4-butanediol diacetate passes through the tube unchanged under these conditions.

EXAMPLE 4

This example is included to demonstrate the deleterious effect of using the subject catalysts modified by treatment with strong acid.

The tube reactor is charged with a catalyst prepared by impregnating the silica-alumina described in Example 1 with 10% by weight of sulfuric acid. After calcining at 400°, the catalyst bed is maintained at 220° C while the feedstock described in Example 1 is passed into the boiler. The initial level of conversion is about the same as with the unmodified catalyst. The activity rapidly falls off, however, and in addition the pellets darken and disintegrate.

EXAMPLE 5

The reactor and catalyst bed described in Example 1 is maintained at 220° C while essentially pure 4-acetoxybutanol (obtained by fractional distillation of its mixture with 1,4-butanediol and 1,4-butanediol diacetate) is passed into the boiler at 36 ml per hour. After a steady state is achieved (3 hours), the effluent is composed of tetrahydrofuran and acetic acid in 1:1 ratio.

It should, of course, be apparent to those skilled in the art that changes may be made in the particular embodiments of the invention described which are within the full intended scope of the invention as defined by the appended claims.

What is claimed is:

1. A process for preparing tetrahydrofuran which comprises heating a carboxylic acid monoester of 1,4-butanediol in the vapor phase in the presence of a dehydroacyloxylation catalyst selected from the group consisting of alumina, silica, silica-alumina, and silica-magnesia under substantially anhydrous conditions at a temperature in the range of from 200° C to about 325° C.

2. The process of claim 1 in which the carboxylic acid monoester of 1,4-butanediol is 4-acetoxybutanol.

* * * * *